(12) United States Patent
Suzuki et al.

(10) Patent No.: US 8,476,478 B2
(45) Date of Patent: Jul. 2, 2013

(54) PROCESS FOR PRODUCING HYDROGENOLYSIS PRODUCTS OF POLYHYDRIC ALCOHOLS

(75) Inventors: Nobuyoshi Suzuki, Wakayama (JP); Masazumi Tamura, Wakayama (JP); Yohei Yoshikawa, Wakayama (JP); Taku Mimura, Wakayama (JP); Masakatsu Takahashi, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/398,377

(22) Filed: Feb. 16, 2012

(65) Prior Publication Data
US 2012/0142976 A1    Jun. 7, 2012

Related U.S. Application Data

(63) Continuation of application No. 12/595,707, filed as application No. PCT/JP2008/056766 on Apr. 4, 2008, now Pat. No. 8,188,321.

(30) Foreign Application Priority Data

Apr. 17, 2007 (JP) .................................. 2007-108500
Jan. 21, 2008 (JP) .................................. 2008-010677

(51) Int. Cl.
*C07C 29/60* (2006.01)
*C07C 29/132* (2006.01)

(52) U.S. Cl.
USPC ...................................................... 568/861

(58) Field of Classification Search
USPC ...................................................... 568/861
See application file for complete search history.

(56) References Cited

U.S. PATENT DOCUMENTS 7,355,083 B2    4/2008    Tuck et al.
8,158,834 B2    4/2012    Suzuki et al.

FOREIGN PATENT DOCUMENTS

| JP | 2 251245 | 10/1990 |
| JP | 8 188544 | 7/1996 |
| WO | 2005 095536 | 10/2005 |
| WO | 2007 010299 | 1/2007 |

OTHER PUBLICATIONS

Li et al., Tianranqi Huagong, 16 (6), pp. 11-14, (1991); abstract only.*
English Translation of International Preliminary Report on Patentability Issued in PCT/JP2008/056766.
Japanese Office Action issued in corresponding Japanese Patent Application No. 2008-010677 dated Mar. 12, 2013 with English translation (6 pp.).

* cited by examiner

*Primary Examiner* — Elvis O Price
(74) *Attorney, Agent, or Firm* — Oblon, Spivak, McClelland, Maier & Neustadt, L.L.P.

(57) ABSTRACT

The present invention relates to a process for producing hydrogenolysis products of polyhydric alcohols with a good selectivity and a high yield, as well as hydrogenolysis catalysts used in the production process. The present invention provides (1) a process for producing a hydrogenolysis product of a polyhydric alcohol which includes the step of reacting the polyhydric alcohol with hydrogen in the presence of a catalyst containing a copper component, wherein the catalyst is a catalyst (A) containing the copper component, an iron component and an aluminum component, or a catalyst (B) containing the copper component and a silicon component; and (2) a hydrogenolysis catalyst for polyhydric alcohols which includes a copper component, an iron component and an aluminum component, and (3) a hydrogenolysis catalyst for polyhydric alcohols which includes a copper component and a silicon component.

18 Claims, No Drawings

PROCESS FOR PRODUCING HYDROGENOLYSIS PRODUCTS OF POLYHYDRIC ALCOHOLS

CROSS-REFERENCE TO RELATED APPLICATIONS

The present application is continuation of U.S. Ser. No. 12/595,707, filed Oct. 13, 2009, which is a National Stage (371) of PCT/JP08/56766, filed Apr. 4, 2008, and claims priority to JP 2007-108500, filed Apr. 17, 2007, and JP 2008-010677, filed Jan. 21, 2008.

FIELD OF THE INVENTION

The present invention relates to a process for producing hydrogenolysis products from polyhydric alcohols with a good selectivity and a high yield as well as hydrogenolysis catalysts used therein.

BACKGROUND OF THE INVENTION

Hydrogenolysis of polyhydric alcohols obtained from the natural world using a catalyst for converting the polyhydric alcohols into other compounds is an important technique from the viewpoint of effective utilization of materials or substances.

On the other hand, the amount of glycerol produced which is used as a polyhydric alcohol in food or medical applications has increased year by year. One of the reasons therefor is spread of bio-diesel fuels which have recently come to prevail owing to uncertain supply of fossil fuels or global warming problems. Glycerol is produced in the course of the process for production of the bio-diesel fuels from raw vegetable materials. However, excessive supply of the glycerol has occurred due to currently limited applications thereof. Therefore, effective utilization of the glycerol has been demanded. As one solution, catalytic reaction of the glycerol into C3 alcohols has been noticed over the world.

The C3 alcohols are useful as various industrial materials, etc. Among the C3 alcohols, there are 1,3-propanediol and 1,2-propanediol as diols. The 1,3-propanediol has been noticed as a raw material of polyesters and polyurethanes, etc.

On the other hand, the 1,2-propanediol has been used, for example, for production of polyester resins, paints, alkyd resins, various plasticizers, anti-freezing fluids, brake oils, etc., and further are useful for production of food wetting agents, viscosity enhancing agents for fruit juices, cellophane softeners for food, cosmetics, drugs, etc.

Hitherto, there have been known and proposed various methods for producing 1,2-propanediol (hereinafter occasionally referred to merely as "1,2-PD") by hydrogenolysis of glycerol.

For example, as the hydrogenolysis using a catalyst, there are known (1) the method using a Ni—Re/C catalyst (for example, refer to Patent Document 1), (2) the method using a Ru/C catalyst (for example, refer to Patent Document 2), (3) the method using a Cu—Zn/Al$_2$O$_3$ catalyst (for example, refer to Patent Document 3), (4) the method using a Cu—ZnO catalyst (for example, refer to Patent Document 4), and (5) the method using a Cu—Cr catalyst (for example, refer to Non-Patent Document 1).

However, these methods are still unsatisfactory because of low conversion rate of glycerol, low selectivity to 1,2-PD, etc.

In addition, there are conventionally unknown any methods using a catalyst containing a copper component, an iron component and an aluminum component or a catalyst containing a copper component and a silicon component as a catalyst for hydrogenolysis of glycerol.

Patent Document 1: PCT Pamphlet WO 03/035582
Patent Document 2: EP 523014A
Patent Document 3: EP 523015A
Patent Document 4: DP 4302464A
Non-Patent Document 1: Applied Catalysis A: General, 281, 225, (2005)

SUMMARY OF THE INVENTION

The present invention relates to a process for producing hydrogenolysis products of polyhydric alcohols with a good selectivity and a high yield, as well as hydrogenolysis catalysts used in the production process.

The present inventors have found that the above technical task can be achieved by using a catalyst (A) containing a copper component, an iron component and an aluminum component, or a catalyst (B) containing a copper component and a silicon component as a catalyst for hydrogenolysis of polyhydric alcohols.

Thus, the present invention relates to the following aspects (1) to (3):

(1) A process for producing a hydrogenolysis product of a polyhydric alcohol, which includes the step of reacting the polyhydric alcohol with hydrogen in the presence of a catalyst containing a copper component, wherein the catalyst is a catalyst (A) containing the copper component, an iron component and an aluminum component, or a catalyst (B) containing the copper component and a silicon component;

(2) a hydrogenolysis catalyst for polyhydric alcohols which includes a copper component, an iron component and an aluminum component; and (3) a hydrogenolysis catalyst for polyhydric alcohols which includes a copper component and a silicon component.

EFFECT OF THE INVENTION

In accordance with the present invention, there are provided a process for producing a hydrogenolysis product of a polyhydric alcohol, in particular, producing 1,2-PD from glycerol, using a catalyst (A) containing a copper component, an iron component and an aluminum component or a catalyst (B) containing a copper component and a silicon component with a good selectivity and a high yield; and hydrogenolysis catalysts used in the production process. In addition, these catalyst are capable of being recovered and reused.

DETAILED DESCRIPTION OF THE INVENTION

In the process for producing a hydrogenolysis product of a polyhydric alcohol according to the present invention, the polyhydric alcohol and hydrogen are heated in the presence of a hydrogenolysis catalyst to hydrogenolyze the polyhydric alcohol.

The polyhydric alcohol is preferably a compound having 2 to 6 hydroxyl groups. Examples of the polyhydric alcohol include aliphatic or alicyclic polyhydric alcohols having 2 to 60 carbon atoms. Specific examples of the polyhydric alcohol include ethylene glycol, diethylene glycol, triethylene glycol, polyethylene glycol, various propanediols, various dipropanediols, various tripropanediols, various butanediols, various dibutanediols, various pentanediols, various pentanetriols, various hexanediols, various hexanetriols, glycerol, diglycerol, triglycerol, various cyclohexanediols, various cyclohexanetriols, pentaerythritol, trimethylol propane, and sugar alcohols such as sorbitol and mannitol. Among these polyhydric alcohols, glycerol is especially preferred from the industrial viewpoint.

The hydrogenolysis product of the polyhydric alcohol used herein means such a compound obtained by reacting the polyhydric alcohol with hydrogen to decompose hydroxyl groups thereof to such an extent that at least one of the hydroxyl groups remains in a non-decomposed state. For example, the hydrogenolysis product of glycerol (number of hydroxyl groups in molecule: 3) includes C3 diols (number of hydroxyl groups in molecule: 2) and C3 monools (number of hydroxyl groups in molecule: 1).

The hydrogenolysis catalyst used in the present invention is the catalyst (A) containing a copper component, an iron component and an aluminum component, or the catalyst (B) containing a copper component and a silicon component.

In the catalyst (A) containing a copper component, an iron component and an aluminum component, the ratio between contents of the copper component, the iron component and the aluminum component in the catalyst (A) (copper component/iron component/aluminum component) is preferably 1/[0.02 to 2.5]/[0.5 to 5.0] and more preferably 1/[0.4 to 2.5]/[1.0 to 4.0] in terms of an atomic ratio between the respective metal elements, from the viewpoint of good catalytic activity (such as conversion rate of the polyhydric alcohol and selectivity to the hydrogenolysis product).

Also, examples of the silicon component contained in the catalyst (B) containing the copper component and the silicon component include silica (silicon dioxide), zeolites of Y-type, A-type, X-type, L-type, etc., mordenite, and compounds having a structure of a condensed acid of silicates such as ZSM-5.

Examples of the catalyst (B) containing the copper component and the silicon component include copper/silica, copper/Y-type zeolite, copper/A-type zeolite, copper/X-type zeolite, copper/L-type zeolite, copper/mordenite, copper/H-ZSM-5 and copper/silica-alumina. Among these catalysts (B), especially preferred are copper/silica, copper/Y-type zeolite, copper/A-type zeolite, copper/X-type zeolite and copper/L-type zeolite.

In particular, the catalyst (B) containing the copper component and the silicon component is preferably in the form of a catalyst obtained by supporting copper on a carrier composed of a silicon-containing compound such as silica and zeolite. Such a catalyst is capable of exhibiting a sufficient catalytic effect even without incorporating a transition metal element other than copper thereinto. However, the other transition metal may also be incorporated into the catalyst to such an extent that the addition thereof adversely affect the aimed effects of the present invention. Examples of the other transition metal include titanium, zinc, molybdenum, manganese, tungsten, ruthenium, nickel, cobalt, iridium, zirconium, yttrium, platinum, cesium and palladium.

The specific surface area of the carrier is preferably from 30 to 1000 m$^2$/g, more preferably from 100 to 900 m$^2$/g and most preferably from 150 to 800 m$^2$/g.

The content of copper atom in the catalyst is preferably from 0.1 to 70% by mass, more preferably from 1 to 60% by mass and most preferably from 5 to 60% by mass.

The content of silicon atom in the catalyst is preferably from 45 to 10% by mass, more preferably from 40 to 15% by mass and most preferably from 30 to 20% by mass.

The ratio between contents of the copper component and the silicon component in the catalyst is controlled such that the atomic ratio of Cu to Si (Cu atom/Si atom) is from about 1/0.1 to about 1/100, preferably from 1/0.3 to 1/20 and more preferably from 1/0.4 to 1/5.

Also, the ratio between contents of the silicon component and the aluminum component in the zeolites is controlled such that the atomic ratio of Si to Al (Si atom/Al atom) is from about 1 to 150, preferably from 15 to 100 and more preferably from 30 to 50.

Among the zeolites, especially preferred is Y-type zeolite.

The method of producing the catalysts is not particularly limited. The catalysts may be produced by conventionally known methods, for example, a precipitation method, an alkoxide method, etc.

The amounts of these catalysts used are respectively from 0.01 to 30 parts by mass, preferably from 0.1 to 20 parts by mass and more preferably from 0.3 to 15 parts by mass on the basis of 100 parts by mass of the raw polyhydric alcohol.

Production of Catalyst (A) Containing Copper Component, Iron Component and Aluminum Component The catalyst (A) containing the copper component, the iron component and the aluminum component may be produced, for example, by the following precipitation method.

First, an aqueous solution containing a water-soluble copper compound, a water-soluble iron compound and a water-soluble aluminum compound as a copper source, an iron source and an aluminum source, respectively, is prepared.

Next, into the thus prepared aqueous solution is added an aqueous alkali solution, for example, an aqueous solution containing a hydroxide or carbonate of alkali metals, etc., thereby precipitating hydroxides of the respective metals. After subjecting the resultant mixture to solid-liquid separation, the thus separated precipitate was fully washed with water and then dried, and further subjected to calcination treatment at a temperature of from about 100 to about 1200° C. and preferably from 400 to 900° C.

As a result, a powdery catalyst composed of a mixture of oxides of the respective metals is obtained. If required, the obtained powdery catalyst may be further granulated by conventionally known methods to form granules thereof having an average particle size of from about 0.1 to about 500 µm and preferably from 0.4 to 50 µm. In addition, if required, the thus obtained catalyst composed of oxides of the respective metals may be supported on an appropriate carrier such as, for example, alumina and silica-alumina.

Production of Catalyst (B) Containing Copper Component and Silicon Component

Also, the catalyst (B) containing the copper component and the silicon component may be produced, for example, by the following precipitation method or the following alkoxide method.

In the precipitation method, a copper nitrate aqueous solution is dropped into an alkaline aqueous solution in which silica is dispersed, to precipitate copper hydroxide. After subjecting the resultant mixture to solid-liquid separation, the thus separated precipitate is fully washed with water and then dried, and further subjected to calcination treatment at a temperature of from about 100 to about 1200° C. and preferably from 300 to 900° C. If required, the thus obtained powdery catalyst may be further granulated by conventionally known methods to form granules thereof having a median diameter of from about 0.1 to about 500 µm and preferably from 0.4 to 200 µm.

In the alkoxide method, tetraethoxysilane is dropped into a slurry composed of copper nitrate and ethylene glycol, and then the slurry is subjected to hydrolysis by adding water thereto. After subjecting the resultant mixture to solid-liquid separation, the obtained precipitate is dried and further subjected to calcination treatment at a temperature of from about 100 to about 1200° C. and preferably from 300 to 900° C. If required, the thus obtained powdery catalyst may be further granulated by conventionally known methods to form granules thereof having a median diameter of from about 0.1 to about 500 μm and preferably from 0.4 to 200 μm.

Copper oxide contained in the catalyst (B) containing the copper component and the silicon component preferably has an average primary particle size of from 0.1 to 100 nm, more preferably from 0.5 to 80 nm and most preferably from 1 to 50 nm.

The process for producing the hydrogenolysis product of the polyhydric alcohol according to the present invention is preferably carried out without using any reaction solvent from the viewpoint of facilitated production procedure. However, the hydrogenolysis of the polyhydric alcohol may also be conducted in the presence of the reaction solvent.

The reaction solvent is preferably a protonic solvent. As the reaction solvent, there may be used, for example, at least one solvent selected from the group consisting of water, methanol, ethanol, 1-propanol, 2-propanol, n-butanol, isobutanol, 1,2-propanediol, 1,3-propanediol and ethylene glycol.

The reaction solvent is used in such an amount that the content of the polyhydric alcohol in the resultant solution is preferably 1% by mass or more and more preferably 10% by mass or more.

In the process of the present invention, a raw hydrogen gas may be used directly or in the form of a dilute gas prepared by diluting hydrogen with an inert gas such as nitrogen, argon and helium.

In addition, the hydrogenolysis reaction may be carried out by using additives other than the reaction solvent such as, for example, acids and bases. However, from the viewpoint of simplified production process, the reaction of the present invention is preferably carried out, in particular, without using any additives.

The reaction conditions are not particularly limited, and may be appropriately determined according to kinds of polyhydric alcohol and catalyst used in the reaction, etc. The hydrogen pressure is preferably 30 MPa or less, more preferably from 0.1 to 25 MPa and more preferably from 5 to 18 MPa as measured at ordinary temperature. The reaction temperature of 80° C. or higher is usually sufficient to carry out the hydrogenolysis. From the viewpoints of a good conversion rate of the polyhydric alcohol by hydrogenolysis as well as a good selectivity to the aimed hydrogenolysis product, the reaction temperature is preferably in the range of from 130 to 350° C., more preferably from 180 to 300° C. and still more preferably from 200 to 250° C. In addition, in this invention, ordinary temperature is defined as 20° C.

The hydrogenolysis reaction may be conducted by either a batch method or a continuous method. The reaction apparatus is not particularly limited, and there may be used apparatuses capable of being pressurized such as an autoclave, fixed-bed flow type apparatuses, etc.

In the process for producing the hydrogenolysis product of the polyhydric alcohol according to the present invention, glycerol is preferably used as the polyhydric alcohol. When using glycerol as the polyhydric alcohol, 1,2-PD can be produced as the hydrogenolysis product thereof with a high selectivity.

Also, the present invention provides a hydrogenolysis catalyst for hydrogenolyzing the polyhydric alcohol, which includes a catalyst containing the copper component, the iron component and the aluminum component, or a catalyst containing the copper component and the silicon component.

EXAMPLES

In the following Examples and Comparative Examples, the term "%" means "% by mass" unless otherwise specified.

Example 1

(Production of Copper/Iron/Aluminum-Based Catalyst)

The following procedure was conducted to produce a Cu/Fe/Al-based catalyst having an atomic ratio Cu/Fe/Al of 1/0.8/1.8.

A reactor equipped with a reflux condenser was charged with water (300 g), $CuSO_4 \cdot 5H_2O$ (48 g), $FeSO_4 \cdot 7H_2O$ (46.8 g) and aluminum hydroxide (12.8 g), and the contents in the reactor were heated to 96° C. while stirring. While maintaining an inside of the reactor at a temperature of 95° C.±2° C., the contents in the reactor were allowed to stand for 1 h. Next, while maintaining the same temperature, a solution prepared by dissolving $Na_2CO_3$ (44.8 g) in water (150 g) was dropped into the reactor over about 80 min. Further, while maintaining the inside of the reactor at a temperature of 95° C.±2° C., a solution prepared by dissolving $CuSO_4 \cdot 5H_2O$ (4.8 g) and $Al_2(SO_4)_3 \cdot 16H_2O$ (46.8 g) in water (109.2 g) and a solution prepared by dissolving $Na_2CO_3$ (27.6 g) in water (98.2 g) were dropped at the same time into the reactor. At this time, the former aqueous solution of the metal salts was dropped over 60 min, whereas the latter aqueous solution of the alkali substance was dropped over 30 min. Next, a solution prepared by dissolving $Al_2(SO_4)_3 \cdot 16H_2O$ (23.4 g) in water (53.5 g) was dropped into the reactor over 30 min, and then a solution prepared by dissolving $Na_2CO_3$ (14.3 g) in water (54.9 g) was dropped thereinto over 30 min. Further, a 10% NaOH aqueous solution was dropped into the reactor to adjust a pH of the mixture in the reactor to 10.5. While maintaining a pH of the mixture in the reactor at 10.5, the mixture was aged for 1 h. After completion of the aging, the obtained reaction mixture was subjected to solid-liquid separation. The resultant precipitate was repeatedly washed three times with water in an amount of 450 mL for each time, and then dried at 100° C. The resultant dried product was lightly pulverized, and then calcined in air at 750° C. for 1 h, thereby obtaining a catalyst as desired.

As a result, it was confirmed that the resultant catalyst had a median diameter of 11 μm. Meanwhile, the median diameter of the catalyst was measured using a laser diffraction/scattering type particle size distribution measuring apparatus "LA-700" available from HORIBA, Ltd.

The measurement was conducted in an ethanol solvent under such a condition that the ultrasonic dispersing time was 1 min and no refractive index was set.

(Production of Hydrogenolysis Product)

A 500 mL iron autoclave equipped with a stirrer was charged with 5.6 g of the above-prepared catalyst and 150 g of glycerol, and an inside of the autoclave was replaced with hydrogen. Thereafter, hydrogen was introduced into the autoclave until reaching 10 MPa, and then the contents in the autoclave were heated and reacted with each other at 230° C. under a pressure of from 10 to 15 MPa for 3 h.

After completion of the reaction, the obtained reaction solution was subjected to filtration and then analyzed by $^1$H-NMR under the following conditions to conduct a quantitative determination of the reaction product. In addition, the resultant gas component was collected in a gas bag and then analyzed by gas chromatography under the following conditions to conduct a quantitative determination of the reaction product. As a result, it was confirmed that the conversion rate of glycerol was 95 mol %, and the selectivity to 1,2-PD was 98 mol % (yield based on glycerol: 93 mol %).

[$^1$H-NMR (for solution)]

Apparatus used: NMR apparatus "Mercury 400" available from Varian Inc.; internal standard substance: sodium trimethylsilylpropionate

[Gas Chromatography (for Lower Hydrocarbon Gas)]

Column: "Porapak Q"; 2.1 m×3.2 mmϕ; 80-100 mesh; detector: FID; injection temperature: 200° C.; detector temperature: 200° C.; flow rate of He: 6 mL/min

[Gas Chromatography (for CO, $CO_2$ gas)]

Column: "Molecular Sieve 5A"; detector: FID (with a methanizer fitted between the column and the detector); injection temperature: 80° C.; detector temperature: 80° C.; flow rate of He: 60 mL/min Example 2

(Production of Hydrogenolysis Product)

A 500 mL iron autoclave equipped with a stirrer was charged with the copper/iron/aluminum-based catalyst used in Example 1 and recovered by filtration and 150 g of glycerol, and an inside of the autoclave was replaced with hydrogen. Thereafter, hydrogen was introduced into the autoclave until reaching 10 MPa, and then the contents in the autoclave were heated and reacted with each other at 230° C. under a pressure of from 10 to 15 MPa for 3 h. As a result, it was confirmed that the conversion rate of glycerol was 91 mol %, and the selectivity to 1,2-PD was 97 mol % (yield based on glycerol: 88 mol %).

Example 3

(Production of Copper/Silica Catalyst)

The following procedure was conducted to produce a copper/silica (Cu/silica) catalyst having an atomic ratio Cu/Si of 1/0.8.

A reactor equipped with a reflux condenser was charged with water (350 g), sodium carbonate (35 g) and silica ($SiO_2$) ("Nip-Jel CX-600" available from NIPPON SILICA IND.; specific surface area: 754 m$^2$/g; 11 g). While stirring the contents in the reactor, a copper nitrate aqueous solution prepared by dissolving copper nitrate trihydrate (57 g) in water (320 g) was dropped into the reactor over 1 h.

Thereafter, the contents in the reactor were heated to 90° C. while stirring. While maintaining an inside of the reactor at a temperature of 90° C.±2° C., the contents in the reactor were allowed to stand for 1 h. After completion of the aging, the obtained reaction mixture was subjected to solid-liquid separation. The resultant precipitate was repeatedly washed with water in an amount of 1 L for each time until an electric conductivity of the wash water reached 1 mS/m, and then dried at 120° C. Thereafter, the resultant dried product was calcined in air at 400° C. for 3 h, thereby obtaining a copper/silica catalyst (copper content: 50%). As a result, it was confirmed that the resultant catalyst had a median diameter of 3.7 μm, and copper oxide contained therein had an average primary particle size of 11.2 nm.

Meanwhile, the median diameter was measured using a particle size distribution measuring apparatus "Model: LA-920" available from HORIBA, Ltd. The measurement was conducted in water as a solvent under such a condition that the ultrasonic dispersing time was 1 min and a relative refractive index was set to 1.3.

Also, the average primary particle size was determined as follows. That is, the primary particle sizes were measured using an X-ray diffraction analyzer ("Model: ULTRA X 18VB2-3" available from Rigaku Corporation.; X-ray source: CuK α ray; voltage: 40 kV; current: 120 mA), and the average primary particle size was calculated from the measured values using an analyzing software "MDJ JADE VERSION 5".

(Production of Hydrogenolysis Product)

A 500 mL iron autoclave equipped with a stirrer was charged with the above-prepared copper/silica catalyst (7.5 g) and glycerol (150 g), and an inside of the autoclave was replaced with hydrogen. Thereafter, hydrogen was introduced into the autoclave until reaching 10 MPa, and then the contents in the autoclave were heated and reacted with each other at 230° C. under a pressure of from 10 to 15 MPa for 3 h.

As a result, it was confirmed that the conversion rate of glycerol was 99 mol %, the selectivity to 1,2-PD was 96 mol %, and the yield based on glycerol was 95 mol %.

Example 4

(Production of Copper/Zeolite Catalyst)

The same procedure for production of the catalyst as in Example 1 was repeated except for replacing the silica ($SiO_2$) used in Example 3 with Y-type zeolite ("ZEOLYST-CBV780" available from Zeolyst International Inc.; specific surface area: 780 m$^2$/g; Si atom/Al atom=40), thereby producing a copper/zeolite (Cu/zeolite) catalyst (copper content: 50%). As a result, it was confirmed that the resultant catalyst had a median diameter of 2.6 μm, and copper oxide contained therein had an average primary particle size of 11.2 nm.

(Production of Hydrogenolysis Product)

The hydrogenolysis reaction was conducted in the same manner as in Example 3 except for using the above-prepared copper/zeolite catalyst. As a result, it was confirmed that the conversion rate of glycerol was 91 mol %, the selectivity to 1,2-PD was 96 mol %, and the yield based on glycerol was 87 mol %.

Comparative Example 1

(Production of Hydrogenolysis Product)

The hydrogenolysis reaction was conducted in the same manner as in Example 3 except for using a copper/chromium catalyst commercially available from NIKKI CHEMICAL Co., Ltd., having an atomic ratio Cu/Cr of 1/0.83. As a result, it was confirmed that the conversion rate of glycerol was 87 mol %, and the selectivity to 1,2-PD was 99 mol % (yield based on glycerol: 86 mol %).

Comparative Example 2

(Production of Hydrogenolysis Product)

The hydrogenolysis reaction was conducted in the same manner as in Example 3 except for charging the catalyst used in Comparative Example 1 and recovered by filtration into the 500 mL iron autoclave equipped with a stirrer, and conducting the reaction for 5 h. As a result, it was confirmed that the conversion rate of glycerol was 70 mol %, and the selectivity to 1,2-PD was 99 mol % (yield based on glycerol: 70 mol %).

Comparative Example 3

(Production of Cu—Zn/Titanium Oxide Catalyst)

A reactor was charged with copper nitrate (100 g) and zinc nitrate (30 g), and the contents in the reactor were dissolved in water (2000 g) and then heated while stirring. The reactor was further charged with titanium oxide (33 g) at 50° C., and then a 10% Na$_2$CO$_3$ aqueous solution (546 g) (containing Na$_2$CO$_3$ in an equimolar amount of the metal salts) was dropped thereinto over 1 h. After aging the mixture in the reactor for 1 h, the resultant precipitate was filtered and washed with water, dried at 110° C. for 10 h, and then calcined at 600° C. for 1 h. As a result, it was confirmed that the obtained metal oxide composed of copper-zinc/titanium oxide had an atomic ratio Cu/Zn of 4/1, and the amount of Cu—Zn supported on titanium oxide as a carrier was 50% by mass.

(Production of Hydrogenolysis Product)

The hydrogenolysis reaction was conducted in the same manner as in Example 3 except for using the above-prepared catalyst. As a result, it was confirmed that the conversion rate of glycerol was 63 mol %, and the selectivity to 1,2-PD was 97 mol % (yield based on glycerol: 61 mol %).

The results of the above Examples and Comparative Examples are shown together in Tables 1 and 2.

TABLE 1

| | Examples | | | |
|---|---|---|---|---|
| | 1 | 2 | 3 | 4 |
| Reaction conditions | | | | |
| Catalyst | Copper/iron/aluminum Atomic ratio Cu/Fe/Al = 1/0.8/1.8 | Copper/iron/aluminum Atomic ratio Cu/Fe/Al = 1/0.8/1.8 | Copper/silica Atomic ratio Cu/Si = 1/0.8 | Copper/zeolite Atomic ratio Cu/Si = 1/0.78 |
| Amount of catalyst used (part by mass) (based on 100 parts by mass of glycerol | 3.7 | 3.7 | 5 | 5 |
| Hydrogen pressure [at ordinary temperature] (MPa) | 10 | 10 | 10 | 10 |
| Reaction temperature (° C.) | 230 | 230 | 230 | 230 |
| Reaction time (h) | 3 | 3 | 3 | 3 |
| Results of reaction | | | | |
| Conversion rate of glycerol (mol %) | 95 | 91 | 99 | 91 |
| Selectivity to 1.2-propanediol (mol %) | 98 | 97 | 96 | 96 |
| Yield of 1.2-propanediol (mol %) | 93 | 88 | 95 | 87 |

TABLE 2

| | Comparative Examples | | |
|---|---|---|---|
| | 1 | 2 | 3 |
| Reaction conditions | | | |
| Catalyst | Copper/chromium Atomic ratio Cu/Cr = 1/0.83 | Copper/chromium Atomic ratio Cu/Cr = 1/0.83 | Copper-zinc/titanium oxide Atomic ratio Cu/Zn/Ti = 1/0.25/1.24 |
| Amount of catalyst used (part by mass) (based on 100 parts by mass of glycerol | 5 | 5 | 5 |
| Hydrogen pressure [at ordinary temperature] (MPa) | 10 | 10 | 10 |
| Reaction temperature (° C.) | 230 | 230 | 230 |
| Reaction time (h) | 3 | 5 | 3 |
| Results of reaction | | | |
| Conversion rate of glycerol (mol %) | 87 | 70 | 63 |
| Selectivity to 1.2-propanediol (mol %) | 99 | 99 | 97 |
| Yield of 1.2-propanediol (mol %) | 86 | 70 | 61 |

INDUSTRIAL APPLICABILITY

In the process for producing a hydrogenolysis product of a polyhydric alcohol according to the present invention, the hydrogenolysis product can be produced from the polyhydric alcohol, in particular, 1,2-PD can be produced from glycerol, with a good selectivity and a high yield. Further, the catalysts used in the hydrogenolysis reaction can be recovered and reused.

The invention claimed is:

1. A process for producing a hydrogenolysis product of a polyhydric alcohol, comprising reacting the polyhydric alcohol with hydrogen in the presence of a catalyst containing a copper component, wherein the catalyst is a catalyst (B) comprising the copper component and a silicon component, and wherein said reacting is in a liquid phase.

2. The process according to claim 1, wherein the polyhydric alcohol is a compound having 2 to 6 hydroxyl groups.

3. The process according to claim 1, wherein the polyhydric alcohol is glycerol.

4. The process according to claim 3, wherein the hydrogenolysis product is 1,2-propanediol.

5. The process according to claim 1, wherein the polyhydric alcohol is an aliphatic polyhydric alcohol having 2 to 60 carbon atoms or an alicyclic polyhydric alcohol having 2 to 60 carbon atoms.

6. The process according to claim 1, wherein the polyhydric alcohol is selected from the ground consisting of ethylene glycol, diethylene glycol, triethylene glycol, polyethylene glycol, a propanediol, a dipropanediol, a tripropanediol, a butanediol, a dibutanediol, a pentanediol, a pentanetriol, a hexanediol, a hexanetriol, glycerol, diglycerol, triglycerol, a cyclohexanediol, a cyclohexanetriol, pentaerythritol, trimethylol propane, and a sugar alcohol.

7. The process according to claim 1, wherein the silicon component contained in the catalyst (B) is selected from the group consisting of a Y-type zeolite, an A-type zeolite, a X-type zeolite, a L-type, zeolite, mordenite, and a compound having a structure of a condensed acid of a silicate.

8. The process according to claim 1, wherein the catalyst (B) containing is selected from the group consisting of copper/silica, copper/Y-type zeolite, copper/A-type zeolite, copper/X-type zeolite, copper/L-type zeolite, copper/mordenite, copper/H-ZSM-5 and copper/silica-alumina.

9. The process according to claim 1, wherein the catalyst (B) containing is selected from the group consisting of copper/silica, copper/Y-type zeolite, copper/A-type zeolite, copper/X-type zeolite and copper/L-type zeolite.

10. The process according to claim 1, wherein the copper component of the catalyst (B) is supported copper on a carrier composed of a silicon-containing compound such as silica and zeolite.

11. The process according to claim 1, wherein the catalyst (B) further comprises a transition metal.

12. The process according to claim 11, wherein the transition metal is selected from the group consisting of titanium, zinc, molybdenum, manganese, tungsten, ruthenium, nickel, cobalt, iridium, zirconium, yttrium, platinum, cesium and palladium.

13. The process according to claim 10, wherein the surface area of the carrier ranges from 30 to 1000 m2/g.

14. The process according to claim 1, wherein in the catalyst (B) the content of copper atom in the catalyst ranges from 0.1 to 70% by mass.

15. The process according to claim 1, wherein in the catalyst (B) the content of silicon atom in the catalyst ranges from 45 to 10% by mass.

16. The process according to claim 1, wherein in the catalyst (B) the ratio between the content of the copper component and the content of the silicon component in the catalyst is controlled such that the atomic ratio of Cu to Si (Cu atom/Si atom) ranges from about 1/0.1 to about 1/100.

17. The process according to claim 8, wherein in the catalyst (B) the ratio between contents of the silicon component and the aluminum component in the zeolites is controlled such that the atomic ratio of Si to Al (Si atom/Al atom) is from about 1 to 150.

18. The process according to claim 1, wherein said process is a batch process.

* * * * *